United States Patent [19]

Westerman

[11] 4,190,562
[45] Feb. 26, 1980

[54] IMPROVED WATER ABSORBENT COPOLYMERS OF COPOLYMERIZABLE CARBOXYLIC ACIDS AND ACRYLIC OR METHACRYLIC ESTERS

[75] Inventor: Ira J. Westerman, Strongsville, Ohio

[73] Assignee: The B. F. Goodrich Company, Akron, Ohio

[21] Appl. No.: 784,100

[22] Filed: Apr. 4, 1977

[51] Int. Cl.$^2$ ................ C08F 20/18; C08F 20/44; C08F 20/56
[52] U.S. Cl. .................. 260/17.4 UC; 260/17.4 R; 526/303; 526/317; 526/319; 526/342
[58] Field of Search .............. 260/17.4 UC, 17.4 R; 526/303, 319, 317, 342

[56] References Cited

U.S. PATENT DOCUMENTS

| | | | |
|---|---|---|---|
| 2,789,030 | 4/1957 | Fetscher | 260/17.4 UC |
| 2,798,053 | 7/1957 | Brown | 260/17.4 UC |
| 3,312,640 | 4/1967 | Ferrigno | 260/17.4 UC |
| 4,066,583 | 1/1978 | Spaulding | 526/317 |

*Primary Examiner*—Harold D. Anderson
*Attorney, Agent, or Firm*—J. Hughes Powell, Jr.

[57] ABSTRACT

Polymers of unsaturated copolymerizable carboxylic acids, at least one acrylic or methacrylic ester containing an alkyl of 10 to 30 carbon atoms, and copolymerizable acrylic or methacrylic nitrile or amide, optionally with a small amount of a cross-linking agent, rapidly absorb and retain large quantities of water and ionic fluids, and are useful in disposable nonwoven articles.

18 Claims, No Drawings

IMPROVED WATER ABSORBENT COPOLYMERS OF COPOLYMERIZABLE CARBOXYLIC ACIDS AND ACRYLIC OR METHACRYLIC ESTERS

BACKGROUND OF THE INVENTION

U.S. Pat. No. 3,915,921 discloses copolymers of unsaturated carboxylic acid monomers with an alkyl acrylate ester wherein the alkyl group contains about 10 to 30 carbon atoms that are efficient water thickeners, which when neutralized by basic materials have improved resistance to loss in viscosity, even in the presence of substantial amounts of inorganic salts such as sodium chloride. These copolymers absorb water, but copolymers having improved rates of water absorption and retention are desired.

SUMMARY OF THE INVENTION

Copolymers of about 40 to 87 weight percent of unsaturated copolymerizable carboxylic acid monomers, about 2 to about 20 weight percent of at least one acrylic or methacrylic acid ester wherein an alkyl group contains 10 to 30 carbon atoms and about 5 to 30 weight percent of at least one acrylic or methacrylic nitrile or amide, optionally with a small amount of a cross-linking agent, rapidly absorb and retain large quantities of water and also absorb and retain ionic aqueous fluids.

DETAILED DESCRIPTION

The copolymers of carboxylic acid monomer and the two acrylic esters of the types and in the amounts defined hereinafter provide a much faster rate of absorption of water and aqueous ionic fluids than copolymers not containing these essential comonomers in the amounts set forth. The copolymers also demonstrate improved retention of absorbed fluid as compared to prior art polymers. The copolymers are readily prepared by copolymerizing the essential monomers, and optionally other comonomers as defined, by free radical polymerization systems. These copolymers have weight average molecular weights from about 10,000 to greater than 1,000,000. Normally, the molecular weights are from about 50,000 to 900,000. Molecular weights of cross-linked polymers may be higher.

The carboxylic monomers useful in the production of the polymers of this invention are the olefinically-unsaturated carboxylic acids containing at least one activated carbon-to-carbon olefinic double bond, and at least one carboxyl group, that is, an acid containing an olefinic double bond which readily functions in polymerization because of its presence in the monomer molecule either in the alpha-beta position with respect to a carboxyl group thusly,

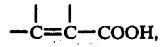

or as a part of a terminal methylene grouping thusly, $CH_2=C<$ present in the copolymer in amounts from about 40 to 87 weight percent of the copolymer. In the alpha-beta acids the close proximity of the strongly polar carboxyl group to the double-bonded carbon atoms has a strong activation influence rendering the substances containing this structure very readily polymerizable. The presence of a terminal methylene grouping in a carboxylic monomer makes this type of compound much more easily polymerizable than if the double bond were intermediate in the carbon structure. Olefinically-unsaturated acids of this class include such widely divergent materials as the acrylic acids typified by acrylic acid itself, methacrylic acid, ethacrylic acid, alpha-chloroacrylic acid, alpha-cyano acrylic acid, beta methyl-acrylic acid (crotonic acid), alpha-phenyl acrylic acid, beta-acryloxy propionic acid, sorbic acid, alpha-chloro sorbic acid, angelic acid, cinnamic acid, p-chloro-cinnamic acid, beta-styryl acrylic acid (1-carboxy-4-phenyl butadiene-1,3), itaconic acid, citraconic acid, mesaconic acid, glutaconic acid, aconitic acid, maleic acid, fumaric acid, and tricarboxy ethylene. As used herein, the term "carboxylic acid" includes the polycarboxylic acids and those acid anhydrides, such as maleic anhydride, wherein the anhydride group is formed by the elimination of one molecule of water from two carboxyl groups located on the same polycarboxylic acid molecule. Maleic anhydride and the other acid anhydrides useful herein have the general structure

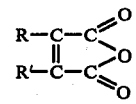

wherein R and R' are selected from the group consisting of hydrogen, halogen and cyanogen ($-C\equiv N$) groups and alkyl, aryl, alkaryl, aralkyl, and cycloalkyl groups such as methyl, ethyl, propyl, octyl, decyl, phenyl, tolyl, xylyl, benzyl, cyclohexyl and the like.

The preferred carboxylic monomers for use in this invention used in amounts of 40 to 87 weight percent total of the monomers polymerized are the monoolefinic acrylic acids having the general structure

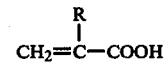

wherein R is a substituent selected from the class consisting of hydrogen, halogen, and the cyanogen ($-C\equiv N$) groups, monovalent alkyl radicals, monovalent aryl radicals, monovalent aralkyl radicals, monovalent alkaryl radicals and monovalent cycloaliphatic radicals. Of this class, acrylic and methacrylic acid are most preferred because of generally lower cost, ready availability, and ability to form superior polymers. Another useful carboxylic monomer is maleic anhydride or the acid.

The preferred acrylic ester monomers having long chain aliphatic groups are derivatives of an acrylic acid represented by the formula

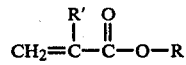

wherein R is an alkyl group having from 10 to 30 carbon atoms, preferably 10 to 20 carbon atoms and R' is hydrogen or a methyl or ethyl group present in the copolymer in amount from about 2 to 20 weight percent, more preferably, about 5 to 15 weight percent. Representative higher alkyl acrylic esters are decyl acrylate, isodecyl methacrylate, lauryl acrylate, stearyl acrylate, behenyl acrylate and melissyl acrylate and the corresponding methacrylates. Mixtures of two or three or more long chain acrylic esters may be successfully polymerized with one of the carboxylic monomers to provide useful thickening resins of this invention. Particularly useful are those methacrylates where the alkyl group contains 16 to 21 carbon atoms present in amounts of about 5 to 15 weight percent of the total monomers. Outstanding polymers have been made with 15±5 weight percent isodecyl methacrylate, 10±3 weight percent lauryl methacrylate, 7±3 weight percent stearyl methacrylate.

The other essential comonomers are acrylic nitriles or amides used in amounts of about 5 to 30 weight percent.

The acrylic nitriles, alpha,beta-olefinically unsaturated nitriles useful in the interpolymers embodied herein are preferably the monoolefinically unsaturated nitriles having from 3 to 10 carbon atoms such as acrylonitrile, methacrylonitrile, ethancrylonitrile, chloroacrylonitrile, and the like. Most preferred are acrylonitrile and methacrylonitrile. The amounts used are from about 5 to 30 weight percent of the total monomers copolymerized.

The acrylic amides include monoolefinically unsaturated amides which may be incorporated in the interpolymers of this invention having at least one hydrogen on the amide nitrogen and the olefinic unsaturation is alpha-beta to the carbonyl group. The preferred amides have the structure

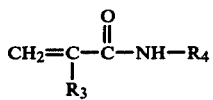

wherein $R_3$ is a member of the group consisting of hydrogen and an alkyl group having from 1 to 4 carbon atoms and $R_4$ is a member of the group consisting of hydrogen and an alkyl group having from 1 to 6 carbon atoms. Representative amides include acrylamide, methacrylamide, N-methyl acrylamide, N-t-butyl acrylamide, N-cyclohexyl acrylamide, N-ethyl acrylamide and others. Very much preferred are acrylamide and methacrylamide used in amounts from about 5 to 30 weight percent of the total monomers copolymerized.

Other acrylic amides include N-alkylol amides of alpha,beta-olefinically unsaturated carboxylic acids including those having from 4 to 10 carbon atoms such as N-methylol acrylamide, N-ethanol acrylamide, N-propanol acrylamide, N-methylol methacrylamide, N-ethanol methacrylamide, N-methylol maleimide, N-methylol maleamide, N-methylol maleamic acid, N-methylol maleamic acid esters, the N-alkylol amides of the vinyl aromatic acids such as N-methylol-p-vinyl benzamide, and the like and others. The preferred monomers of the N-alkylol amide type are the N-alkylol amides of alpha,beta-monoolefinically unsaturated monocarboxylic acids and the most preferred are N-methylol acrylamide and N-methylol methacrylamide used in amounts of about 5 to 20 weight percent.

N-alkoxymethyl acrylamides also may be used having the structure

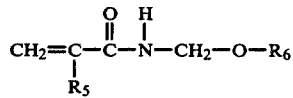

wherein $R_5$ is selected from the group consisting of hydrogen and methyl, and $R_6$ is an alkyl group having from 1 to 8 carbon atoms. It is thus intended that where references are made herein regarding the essential N-substituted alkoxymethyl amides, the term "acrylamide" includes "methacrylamide" within its meaning. The preferred alkoxymethyl acrylamides are those wherein $R_6$ is an alkyl group containing from 2 to 5 carbon atoms and useful is N-butoxymethyl acrylamide.

The preferred cross-linking monomer for use in preparing the copolymers, if one is employed, is a polyalkenyl polyether having more than one alkenyl ether grouping per molecule. The most useful possess alkenyl groups in which an olefinic double bond is present attached to a terminal methylene grouping, $CH_2{=}C<$. They are made by the etherification of a polyhydric alcohol containing at least 4 carbon atoms and at least 3 hydroxyl groups. Compounds of this class may be produced by reacting an alkenyl halide, such as allyl chloride or allyl bromide with a strongly alkaline aqueous solution of one or more polyhydric alcohols. The product is a complex mixture of polyethers with varying numbers of ether groups. Analysis reveals the average number of ether groupings on each molecule. Efficiency of the polyether cross-linking agent increases with the number of potentially polymerizable groups on the molecule. It is preferred to utilize polyethers containing an average of two or more alkenyl ether groupings per molecule. Other cross-linking monomers include for example, diallyl esters, dimethallyl ethers, allyl or methallyl acrylates and acrylamides, tetraallyl tin, tetravinyl silane, polyalkenyl methanes, diacrylates and dimethacrylates, divinyl compounds as divinyl benzene, polyallyl phosphate, diallyloxy compounds and phosphite esters and the like. Typical agents are allyl pentaerythritol, allyl sucrose, trimethylolpropane triacrylate, 1,6-hexanediol diacrylate, pentaerythritol triacrylate, tetramethylene dimethacrylate, tetramethylene diacrylate, ethylene diacrylate, ethylene dimethacrylate, triethylene glycol dimethacrylate, and the like. Allyl pentaerythritol and allyl sucrose provide excellent polymers in amounts less than 0.5 weight percent. Cross-linking of the polymers provides improved ability for the copolymers to swell under a confining pressure.

When the optional cross-linking agent is present, polymeric mixtures containing about 0 to about 3% by weight of cross-linking monomer based on the total of carboxylic acid monomer plus the alkyl acrylate ester monomers, and more preferably, 0.1 to 0.5 weight percent or phm.

Another method to obtain the desired cross-linking is to use a comonomer which can react to yield cross-links during polymerization. Examples are 2-hydroxyethyl methacrylate and hydroxypropyl methacrylate, and the like. These units, when copolymerized, cross-link by interchain esterification with carboxylic groups. For 2-hydroxyethyl methacrylate, about 1 to 7 weight percent of monomers based on the total weight of monomers will provide a desired degree of cross-linking.

Another method of obtaining cross-lihked polymers is by reacting small amounts of a polyvalent base with the carboxyl-containing polymer. Those materials which yield multivalent cations, for example, include calcium, magnesium, zinc, and aluminum. A mixed salt to be used would be one containing potassium or sodium ions with small amounts of calcium or aluminum ions, for example, to provide the multivalent cation to provide cross-linking through polymeric carboxyl groups.

It will also be understood that small amounts of other vinylidene monomers, that is, those copolymerizable monomers containing at least one terminal $CH_2<$ group may also be included as a copolymerizable monomer with the essential monomers so long as such monomers do not adversely affect the desired balance of water absorption and retention of the polymeric materials. Such materials include vinyl acetate, vinyl pyrrolidone, methyl vinyl ether, ethyl vinyl ether, methyl vinyl ketone and like in amounts less than about 10 weight percent of the polymer, normally less than 5 weight percent.

The polymers of this invention are preferably made by polymerization in an inert diluent having some solubilizing action on one or more of the monomeric ingredients but substantially none on the resultant polymer. Polymerization in mass may be employed but is not preferred because of the difficulty in working up the solid polymeric masses obtained. Polymerization in an aqueous medium containing a water-soluble free radical catalyst peroxygen is useful. Polymerization in an organic liquid which is a solvent for the monomers but a non-solvent for the polymer, or in a mixture of such solvents, in the presence of a solvent-soluble catalyst is most preferred because the product is usually obtained as a very fine friable and often fluffy precipitate which, after solvent removal, seldom requires grinding or other treatment before use. Suitable solvents for the latter method include benzene, xylene, tetralin, hexane, heptane, carbon tetrachloride, methyl chloride, ethyl chloride, bromo trichloro methane, dimethyl carbonate, diethyl carbonate, ethylene dichloride, and mixtures of these and other solvents.

The polymerizations desirably are conducted in the presence of a haloethane or halomethane, preferably containing at least four halogen atoms. Representative materials include for example, a fluoroethane, fluoromethane, chlorofluoromethane, bromofluoroethane, or preferably a chlorofluoroethane or chlorofluoromethane containing at least four halogen atoms including, for example, 1,1,2-trichloro-1,2,2-trichloroethane, trichlorofluoromethane, tetrafluoromethane, chlorotrifluoromethane, bromotrifluoromethane, 1-chloro-1,1,2,2,2-pentafluoroethane, dichlorodifluoromethane, 1,2-difluoro-1,1,2,2-tetrachloroethane and the like. The amounts of these materials used may be varied from the amount just sufficient to make a slurry of the reactants up to where there is a substantial excess of the chlorofluoroethane, as will be apparent to those skilled in the art. Preferred diluents are those which are solvents for the monomers but nonsolvents for the polymers.

Polymerization in the diluent medium is carried out in the presence of a free radical catalyst in a closed vessel in an inert atmosphere and under autogenous pressure or artificially-induced pressure or in an open vessel under reflux at atmospheric pressure. Temperature of the polymerization may be varied from 0° C. to 100° C., depending to a large degree on the molecular weight desired in the polymer. Polymerization under reflux at 50° to 90° C. under atmospheric pressure using a free radical catalyst is generally effective in bringing a polymer yield of 75% to 100% in less than 10 hours. Suitable catalysts include peroxygen compounds such as sodium, potassium and ammonium persulfates, caprylyl peroxide, benzoyl peroxide, hydrogen peroxide, pelargonyl peroxide cumene hydroperoxides, tertiary butyl diperphthalate, tertiary butyl perbenzoate, sodium peracetate, sodium percarbonate, and the like as well as azo diisobutyryl nitrile, hereinafter referred to as azoisobutyronitrile. Other catalysts utilizable are the so-called "redox" type of catalyst and the heavy-metal activated catalyst systems.

These polymers generally do not attain their maximum properties until converted to a partial alkali, ammonium or amine salt. The neutralizing agent is preferably a monovalent alkali such as sodium, potassium, lithium or ammonium hydroxide or the carbonates and bicarbonates thereof, or mixtures of the same, and also amine bases having not more than one primary or secondary amino group. Such amines include, for example, triethanolamine, ethanolamine, isopropanolamine, triethylamine, trimethyl amine, and the like.

At least 30% of the acid, carboxyl, groups are neutralized to an ionic state, that is, $-CO_2^- M^+$. Preferably, about 50 to 90 weight percent of the acid groups are neutralized to $-CO_2M$. The counter ion $M^+$ is the alkali cation $Li^+$, $K^+$, the ammonia ion $NH_4^+$ or quaternary cationic compounds resulting from the neutralization with an organic amine. Excellent results have been obtained with $Na^+$ and $K^+$. Neutralization with triethanolamine has been particularly useful.

As water absorbent materials these polymers find many uses in powder, lump, film, fiber, fabric form and like form. They are of particular utility in the disposable nonwoven industry where there is need for polymers which will absorb and retain water and ionic physiological fluids. An important feature of these polymers is their enhanced thickening property even in the presence of a salt. Specific applications include disposable diapers, medical-surgical supplies and personal care products. Such applications require a polymer which must imbibe the liquid to be absorbed rapidly and be a polymer that will not dissolve. Further, the fluid must be immobilized or congealed in some way to be retained. The materials may also be used as suitable additives to greatly increase the absorptive power of conventional absorbents such as cotton, wood pulp and other cellulosic absorbents used in applications such as wiping cloths, surgical sponges, catamenial devices, and the like. In a specific application, for example, a disposable diaper, there is an inner layer of a soft absorbent nonwoven material that absorbs and passes urine to an inner layer of fluffy fibrous absorbent material, wherein during the construction of this nonwoven fiber agglomerates or fibers of the polymers of this invention may be included and an additional impervious plastic layer, as polyethylene. A film of the copolymers of this invention may be used between the outer plastic layer and the inner fluffy absorbent layer. Use of the polymers of this invention can result in reduction in the bulk size of many disposable nonwovens.

The test for absorbency involves enclosing a weighed polymeric sample within a sewn strip of cheesecloth, the assembly resembling a tea bag. In order to determine the amount of fluid absorbed, a blank cheesecloth bag not containing polymer is treated identically. Both the blank and polymer containing samples are immersed in the fluid, drained for a definite time and weighed. From the weights of the blank and sample after each immersion, the amount of fluid absorbed in a specific time is readily calculated. Powders, fibers, thin films and granules may be tested in this manner. Sample films are cast from a 1% aqueous mucilage of alkali neutralized polymers, and for the Examples a 15 gram sample of a 1% mucilage is placed in an aluminum foil cup 5 cc in diameter and dried at atmospheric pressure at 80° C.

Cheesecloth bags were prepared from 15 mm sq. of cheesecloth folded over and sewn with thread. Samples were placed in the fluid to be absorbed for periods indicated in the data tables with 15 minutes drainage time between each immersion.

The polymers are readily prepared with lauroyl peroxide, t-butyl peroxy pivalate, azoisobutyronitrile and the like in a solvent for the monomer/nonsolvent for the copolymer. The polymers were prepared in batch polymerization at 65° C. in 1,1,2-trichloro-1,2,2-trifluoroethane (Freon 113) as the solvent at 65° C. using caprylyl peroxide as the catalyst. The resulting polymers were isolated and dried for 15 to 20 hours in a vacuum oven at 60° C. The ionic fluid was simulated urine prepared from 97.09 weight percent water, 1.49 weight percent urea, 0.80 weight percent sodium chloride, 0.11 weight percent $MgSO_4 \cdot 7 H_2O$ and 0.06 weight percent $CaCl_2$.

EXAMPLE I

A polymer sample was prepared from 80 weight parts acrylic acid, 15 weight parts acrylonitrile and 5 weight parts stearyl methacrylate in 675 weight parts of Freon 113 in the presence of 0.28 weight parts lauroyl peroxide. A sample of cast ammonium salt film weighing 0.16 gram was tested for water and ionic fluid absorbency. The results obtained and the times of immersion are set forth hereinbelow. The absorbed fluid being expressed as fluid/polymer ratio (weight of fluid absorbed × weight of polymer).

| Immersion Seconds | Distilled Water | Synthetic Urine |
|---|---|---|
| 15 | 54.9 | 30.2 |
| 30 | 99.3 | 38.1 |
| 45 | 139.6 | 41.2 |
| 90 | 170.3 | 41.4 |

These data clearly demonstrate the water absorbency of this polymer. Copolymers with methacrylonitrile will provide comparable results as well as with methacrylic acid rather than acrylic acid.

EXAMPLE II

In this Example a copolymer was made with 10 weight percent acrylamide instead of acrylonitrile to demonstrate the absorption of water reported as amount of water absorbed times the weight of polymer. The polymer was prepared as described in Example I with 7 weight percent of lauryl methacrylate and 83 weight percent acrylic acid and acrylamide. The film weight was 0.15 gram. The absorption data obtained in distilled water is as follows:

| Total Immersion Time - Seconds | |
|---|---|
| 15 | 37.9 |
| 30 | 65.9 |
| 45 | 84.9 |
| 60 | 97.9 |
| 90 | 110.5 |
| 120 | 118.6 |

Comparable results were obtained when the copolymer contains methacrylamide instead of acrylamide. Good water absorbency is also obtained when the copolymer contains an additional 0.02 weight percent of allyl pentaerythritol to provide a lightly cross-linked copolymer. These data are to be compared to a copolymer of 93 weight percent of acrylic acid and 7 weight percent lauroyl methacrylate. Absorbed fluid and the fluid/polymer ratio per distilled water of this polymer at 15 seconds was 13.6; at 30 seconds, 25.6; and at 90 seconds, 46.8.

I claim:

1. A film forming water absorbing interpolymer of monomers comprising (1) from about 40 to 87 weight percent of an olefinically unsaturated carboxylic acid monomer, (2) 2 to 20 weight percent of an acrylic ester monomer of the formula

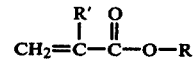

where R' is hydrogen, methyl or ethyl and R is an alkyl group containing 10 to 30 carbon atoms and (3) 5 to 30 weight percent of at least one acrylic or methacrylic nitrile or amide said weight percents based on said interpolymer.

2. An interpolymer of claim 1 containing 0 to 3 weight percent of a cross-linking agent selected from the group consisting of cross-linking monomers and polyvalent bases.

3. An interpolymer of claim 1 wherein (2) is present in amount from about 5 to 15 weight percent and (3) is present in amount from about 5 to 25 weight percent.

4. An interpolymer of claim 3 wherein said carboxylic acid monomer is acrylic acid, (2) is isodecyl methacrylate, lauryl methacrylate or stearyl methacrylate, and (3) is acrylonitrile.

5. An interpolymer of claim 3 wherein said carboxylic acid monomer is acrylic acid, (2) is isodecyl methacrylate, lauryl methacrylate or stearyl methacrylate, and (3) is acrylamide.

6. An interpolymer of claim 3 wherein the polymer contains about 0.01 to 0.5 weight percent cross-links.

7. An interpolymer of claim 5 wherein at least about 30 weight percent of the carboxylic groups are neutralized to

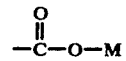

structure wherein M is selected from the group consisting of Li, Na, K, $NH_4$ ions and an amine base having not more than one primary or secondary amino group.

8. An interpolymer of claim 3 wherein the acid is acrylic acid, methacrylic acid or, maleic acid.

9. An interpolymer of claim 6 wherein the cross-linking monomer contains at least a $CH_2=C<$ group and at least one other polymerizable group, said group being an unsaturated nonconjugated bond.

10. An interpolymer of claim 9 wherein said cross-linking monomer is a polyalkenyl polyether of a polyhydric alcohol containing more than one alkenyl ether group per molecule and the polyhydric alcohol contains at least 3 hydroxyl groups in amounts of 0.01 to less than 0.5 weight percent of the total monomers.

11. An interpolymer of claim 10 wherein said monomer is an allyl pentaerythritol.

12. An interpolymer of claim 10 wherein said monomer is an allyl sucrose.

13. An interpolymer of claim 3 containing 7 to 13 weight percent of (2) stearyl methacrylate and (3) is acrylamide.

14. An interpolymer of claim 10 wherein said acid is acrylic acid, (2) is stearyl methacrylate, (3) is acrylonitrile and said cross-linking agent is allyl pentaerythritol in amount from 0.05 to 0.2 weight percent.

15. An interpolymer of claim 2 containing 10 to 20 weight percent of (2) isodecyl methacrylate and (3) is acrylonitrile.

16. An interpolymer of claim 3 wherein (2) is lauryl methacrylate present in amounts of 7 to 13 weight percent and (3) is acrylonitrile.

17. An interpolymer of claim 15 containing 10 to 20 weight percent of (2) isodecyl methacrylate and (2) is acrylamide.

18. An interpolymer of claim 13 containing 10 to 20 weight percent of (2) isodecyl methacrylate and (3) is acrylonitrile.